United States Patent
Italia

[19]

[11] Patent Number: 5,950,504
[45] Date of Patent: Sep. 14, 1999

[54] PIPETTOR ATTACHABLE/INTEGRATEABLE MICROCENTRIFUGE TUBE OPENER

[76] Inventor: James A. Italia, 3715 N. Fremont, Chicago, Ill. 60613

[21] Appl. No.: 09/089,648

[22] Filed: Jun. 3, 1998

[51] Int. Cl.[6] ............................................. B67B 7/44
[52] U.S. Cl. ........................................ 81/3.09; 7/151
[58] Field of Search .................... 81/3.09, 3.4, 3.55; 7/151; D24/222; 422/100; 73/1.74, 432.1

[56] References Cited

U.S. PATENT DOCUMENTS

| | | |
|---|---|---|
| 807,380 | 12/1905 | Hicks . |
| 1,954,422 | 4/1934 | McIntyre . |
| 1,960,531 | 5/1934 | Driscoll . |
| 3,604,290 | 9/1971 | Waite . |
| 4,507,988 | 4/1985 | LoFaso et al. ........................ 81/3.09 |
| 4,542,833 | 9/1985 | DeVaughn . |
| 4,683,782 | 8/1987 | Warburg . |
| 4,704,924 | 11/1987 | Echols . |
| 4,713,219 | 12/1987 | Gerken et al. . |
| 4,723,465 | 2/1988 | Hughes . |
| 4,909,991 | 3/1990 | Oshikubo ............................. 422/100 |
| 4,979,407 | 12/1990 | Hernandez et al. .................. 81/3.09 |
| 5,104,624 | 4/1992 | Labriola ............................... 422/100 |
| 5,253,551 | 10/1993 | DeVaughn . |

FOREIGN PATENT DOCUMENTS

| | | | |
|---|---|---|---|
| 527306 | 10/1956 | Belgium . | |
| 931.226 | 2/1948 | France . | |
| 25 08 499 | 9/1976 | Germany . | |
| 29 11 086 | 10/1979 | Germany . | |
| 309672 | 7/1933 | Italy ..................................... | 7/151 |

OTHER PUBLICATIONS

Catalog Page for USA/Scientific Plastics, Inc., Variable Volume Pippettor published more than one year prior to filing date of application. p. D1, 1995.

*Primary Examiner*—David A. Scherbel
*Assistant Examiner*—Joni B. Danganan
*Attorney, Agent, or Firm*—Dick and Harris

[57] ABSTRACT

A pipettor attachable microcentrifuge tube opener adapted to fit on a common pipettor, allowing the user to open a microcentrifuge tube without the need to open the tube solely by hand or through use of an additional instrument. Alternatively, the features of the microcentrifuge tube opener may be integrated into an originally manufactured pipettor.

16 Claims, 3 Drawing Sheets

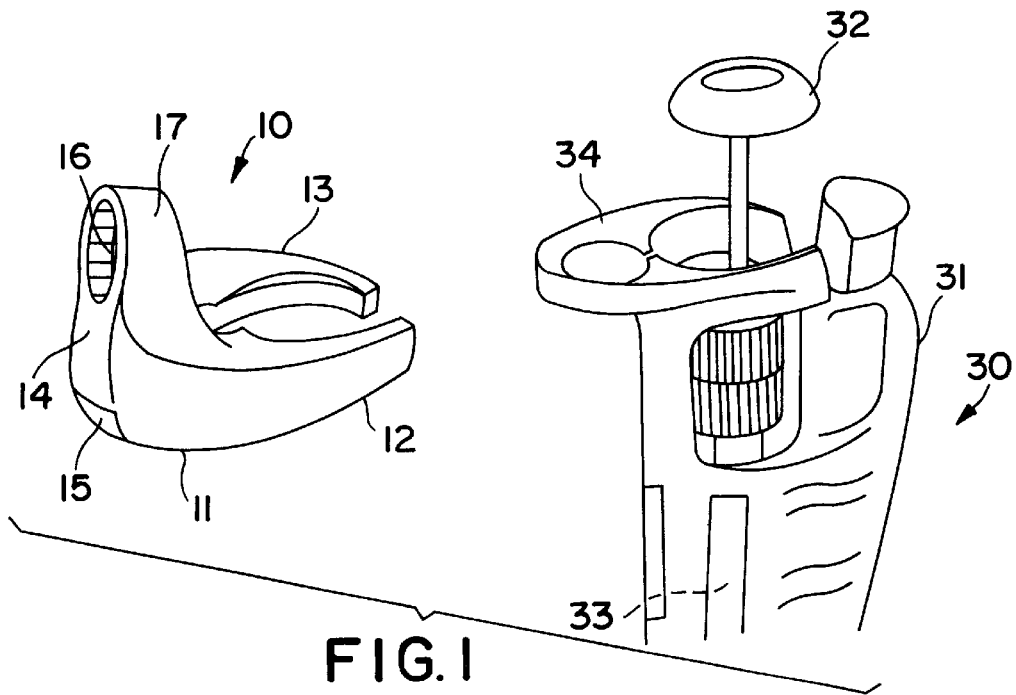
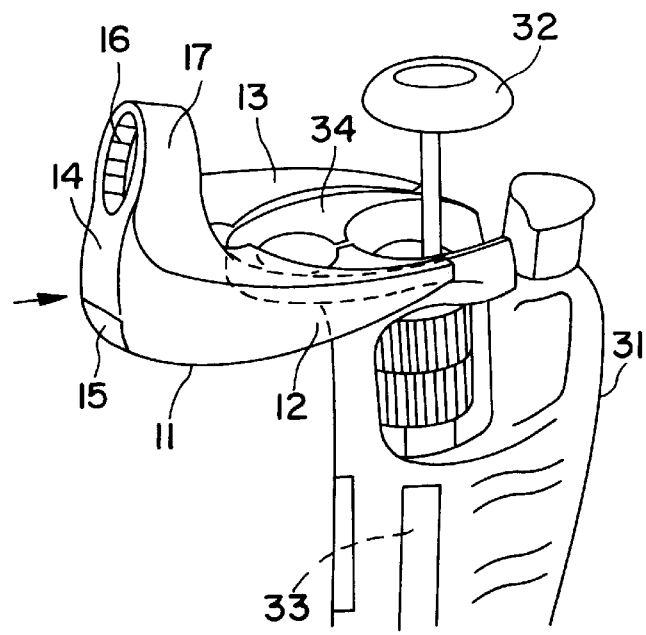
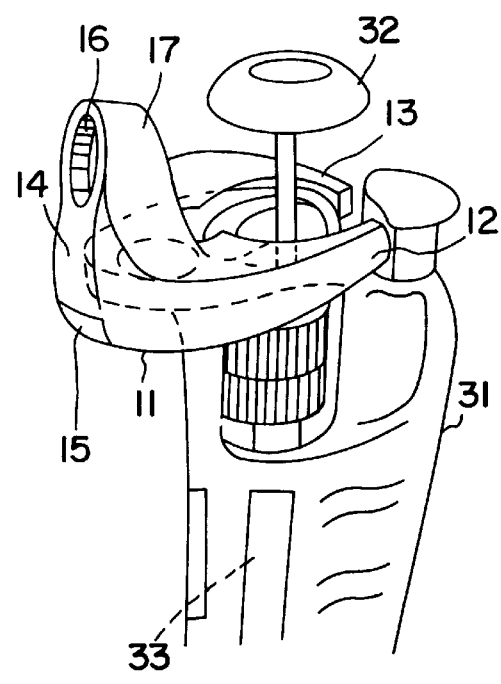
FIG. 1
FIG. 2
FIG. 3

PIPETTOR ATTACHABLE/INTEGRATEABLE MICROCENTRIFUGE TUBE OPENER

BACKGROUND OF THE INVENTION

1. Field of the Invention

The invention is directed to microcentrifuge tube openers, and more particularly a microcentrifuge tube opener attachable to or integrated with a pipettor.

2. Background Art

A microcentrifuge tube is generally a small container often used in medical and science laboratories to hold and control fluids. The tube has an opening on one end of the container and a cap to seal the opening to, in turn, prevent the contents of the container from either leaking to the outside environment or being contaminated by the outside environment. The cap is commonly either a snap cap or screw cap. As is known in the art, the snap cap often has a tab which projects beyond the outer perimeter of the opening of the container, an inner portion shaped to seal the opening, and a connecting strip which acts as a hinge between the cap and the container. A tube is commonly filled by a pipettor, which is comprised of a plunger, a shaft and a handle and is used to draw up or dispense the fluids or liquids from and into the microcentrifuge tubes.

Because of the need to tightly seal the tubes from the outside environment, it is often difficult to open the cap of a tube causing fatigue to an individual when opening a tube by hand. The opening of a tube is further complicated due to the relatively small size of the tube, especially in reference to an individual's hand, which can lead to an individual's hand coming into inadvertent contact with the contents of the tube. Accordingly, various types of tube openers have been developed to ease an individuals opening of a tube and diminish the opportunity of contamination. Typical tube openers are shown in Warburg, U.S. Pat. No. 4,683,78 and DeVaughn, U.S. Pat. No. 5,253,551. While these types of openers may ease the process of opening the microcentrifuge tubes and help prevent possible contamination, they are often not used because the time and effort required to use the standard opener is not outweighed by the benefits from its use.

Because the standard openers are themselves small devices, they are often lost among the laboratories' benches. Once found, in order to use the opener the individual must 1) put down the pipettor; 2) pick up the opener; 3) open the tube; 4) put down the opener; 5) pick up the pipettor; and then 6) use the pipettor to dispense the fluid. The number of steps required to use such openers in combination with the vast number of tubes opened in a day by technicians means that individuals do not waste their time and effort in using such openers, when not required for other reasons, preferring to simply use their hands. Under circumstances where use of such tube openers are required, efficiency may suffer.

Accordingly, it is an object of the present invention to develop a microcentrifuge opener that will be used by individuals.

It is further an object of the present invention to develop a microcentrifuge opener that is capable of being used without the need to put down the pipettor being used to dispense fluids into or out of the tube.

These and other objects of the invention will become apparent in light of the present specification and drawings.

SUMMARY OF THE INVENTION

The invention comprises a pipettor attachable/integrateable microcentrifuge tube opener for the opening of a microcentrifuge tube by removing its cap. The cap may be either of a snap-on type or a screw-on type. If the cap is of the snap-on variety, it will have a tab extending beyond the outer perimeter of the tube. Opening of the cap permits access to the contents within the tube, usually fluids, by a pipettor. The opener consists of a body including a pipettor attachment region on one end and a tube opener region positioned on an opposite end. Within the pipettor attachment region is a securement member capable of attaching and restraining the opener to a pipettor. Similarly, within the tube opener region is a cap engagement member capable of receiving at least a portion of the microcentrifuge tube cap towards restraining the cap in a particular position when the tube is being opened.

The securement member of the opener is preferably a pair of semi-flexible prongs which, in combination, form a substantially U-shaped clasp. The pipettor is preferably positioned through the opening formed by the U-shaped clasp so that the pipettor is at least partially encircled on each side by the pair of semi-flexible prongs for restraining the microcentrifuge tube opener in an operable position on the pipettor.

In one embodiment, the cap engagement member is effectuated by a slot aperture operably positioned in the tube opener region capable of receiving at least a portion of the tab of a snap-on type cap to, in turn, restrain the position of the cap as the tube or pipettor is moved in a manner so that the cap is pulled away from the tube when opening the microcentrifuge tube. Alternatively, the cap engagement member is a substantially circular or semi-circular socket operably positioned to receive at least a portion of the cap's perimeter. In this embodiment, the socket is preferably dimensioned to have a diameter slightly larger than that of the cap. As such, a frictional fit is created between the socket and the cap's outer perimeter so as to restrain the cap's position relative to the tube. After the cap is seated within the socket, the tube may be rotated about its longitudinal axis thereby opening the tube, with the cap capable of being retained in the socket.

In another embodiment, the tube opener region may be substantially perpendicular to the attachment region of the microcentrifuge tube opener so that the tube opener region has an upper end and a lower end. The lower end contains the slot aperture, which is adjacent to the attachment region. Proximate to the upper end is a second cap engagement member. This second cap engagement member may be a substantially circular or semi-circular socket capable of receiving at least a portion of the cap's outer perimeter. In both the semi-circular and circular socket embodiments, the sockets are dimensioned so that the socket's diameter is slightly larger than that of the tube cap's diameter to create a friction fit when the cap is inserted into the sockets where the cap is capable of being retained upon removal from the tube. The attachable microcentrifuge tube opener may be manufactured in accordance with commercial practices and standards and is preferably of semi-flexible, autoclavable plastic-like material.

The invention may also be integrated into a pipettor rather than a separate adaptor or retro-fit to existing pipettors. When the opener is integrated into a pipettor, the pipettor has a longitudinal handle, a plunger and a suction shaft for insertion into the microcentrifuge tube towards dispensing or removing fluids from the tube. The handle has a top and bottom end and is positioned between the plunger and the suction shaft in a manner so that the plunger is adjacent to the top end of the handle and operably connected to the suction shaft, which is adjacent the bottom end of the handle.

Also contained on the handle is at least one microcentrifuge tube opening member.

In one embodiment, the at least one tube opening member is formed from a rim of material overhanging the top end of the handle. Within the rim is at least one slot aperture capable of receiving at least a portion of the tab on the snap-on cap towards restraining the position of the cap when the pipettor or tube is moved in a manner so that the cap is pulled away from the tube so as to open the microcentrifuge tube. The rim of material may also be formed into either a semi-circular or circular socket for receipt of at least a portion of the outer perimeter of the cap. As described above, the socket will, at least partially, encircle the cap's outer perimeter to create a friction fit with the cap towards maintaining the cap's position when the tube is rotated to an open position and so as to be capable of retaining the cap in the socket after removal from the tube.

It is also envisioned that the pipettor may alternatively contain a first and second microcentrifuge tube opening member. In this embodiment, the first microcentrifuge tube opening member is again comprised of at least one slot aperture within a rim of material overhanging the top end of the handle. The second microcentrifuge cap opening member is positioned within a raised upper portion of the rim, where the raised portion of rim is in a plane substantially perpendicular to the flat portion of the rim and in a plane substantially parallel to the handle. The second microcentrifuge tube opening member may be a substantially semi-circular socket or a substantially circular socket. Each of the sockets being dimensioned so that their diameters are slightly larger than the diameter of the cap so that when the cap is inserted into the socket a friction fit is created between the socket and the cap's outer perimeter thereby holding the cap in place. With the cap held in place, the microcentrifuge tube may be opened by rotating it about its longitudinal axis with the cap capable of being retained in the socket.

BRIEF DESCRIPTION OF THE DRAWINGS

FIG. 1 is a front perspective view of the pipettor attachable microcentrifuge tube opener and pipettor prior to attachment to a pipettor;

FIG. 2 is a front perspective view of the pipettor attachable microcentrifuge tube opener in the process of being attached to a pipettor;

FIG. 3 is a front perspective view of the pipettor attachable microcentrifuge tube opener completely attached and secured to a pipettor;

DETAILED DESCRIPTION OF THE DRAWINGS

Figure 4:
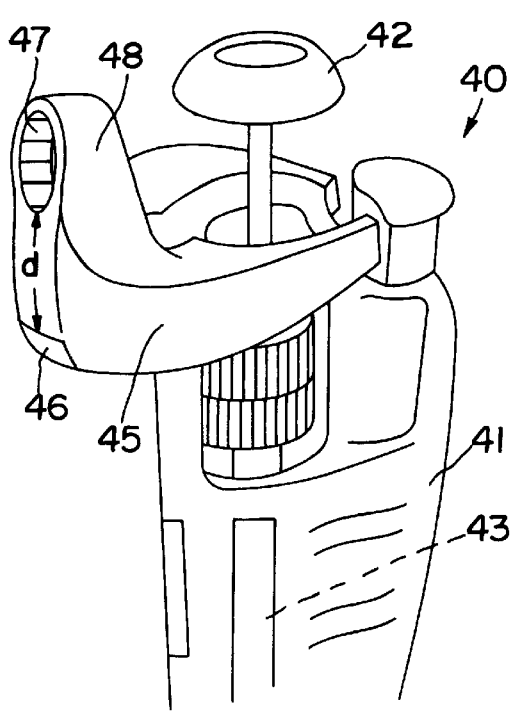
FIG. 4 is a front perspective view of a pipettor having an integrated microcentrifuge tube opener.

While this invention is susceptible of embodiment in many different forms, there is shown in the drawings and will herein be described in detail, one specific embodiment with the understanding that the present disclosure can be considered as an exemplification of the principles of the invention and is not intended to limit the invention to the embodiment illustrated.

Pipettor attachable microcentrifuge tube opening apparatus 10 is shown in FIG. 1 prior to attachment to pipettor 30. Pipettor 30 is of the type known in the art. While depicting a particular type of pipettor in the drawings, it is contemplated that apparatus 10 be used with all varieties of pipettors used and known in the art, such as those manufactured by Gilson, Labsystems, USA/Scientific, Continental Laboratory Products, and others. Each pipettor 30 has handle 31, plunger 32 and suction shaft 33. Suction shaft 33 is inserted into open microcentrifuge tubes for dispensing fluids into or withdrawing fluids out of such tubes.

Pipettor attachable microcentrifuge tube opening apparatus 10 comprises body 11 including attachment region 12–13 and tube opener region 14. It is contemplated that attachment region 12–13 may include a variety of methods for securing apparatus 10 to pipettor 30. In the present embodiment, attachment region is formed out of a pair of semi-flexible and resilient securement prongs 12 and 13. As shown in FIGS. 1 through 3, prongs 12 and 13 are preferably slightly curved so as to form a U-shaped clasp region for receipt of at least a portion of the overhanging rim of material 34 on handle 31 of pipettor 30. Of course, it should be appreciated by those in the art that apparatus 10 may be secured to any portion of handle 31 which does not interfere with the operation of pipettor 30.

Body 11 also includes tube opener region 14. As shown in FIG. 1, tube opener region includes cap engagement means in the form of slot aperture 15. It is common for microcentrifuge tubes having a snap-on type cap to include a tab protruding past the outer perimeter of the tube so as to ease the removal of the cap for opening the tube. As will be recognized, force is exerted on the tab so as to pry the cap off of the tube. Slot aperture 15 is dimensioned so as to be capable of receiving at least a portion of the tab from the tube cap. Tube and pipettor 30 are then moved away from each other with the tab of the cap remaining in slot aperture 15 so as to open the microcentrifuge tube.

It should be appreciated by those in the art that tubes also come with screw-on type caps having no protruding lips. Accordingly, it should be appreciated that slot aperture 15 may be replaced with a substantially circular or semi-circular socket dimensioned for frictional receipt of the outer perimeter of the cap. This type of substantially circular socket 16 is shown in FIG. 1.

Apparatus 10 shown in FIGS. 1 through 3 may also include a second cap engagement means within tube opener region 14. Raised portion 17 of tube opener region 14 contains substantially circular socket 16 appropriately dimensioned for frictional receipt of the cap from the microcentrifuge tube thereby encircling the outer perimeter of the cap. The distance between slot aperture 15 and socket 16 should create a separation so as to permit the use of both slot aperture 15 and socket 16 on two different tubes simultaneously.

Again, socket 16 may be used with screw-on type caps. With the cap being held stationary and in place by socket 16, the tube may then be rotated about its longitudinal axis to screw the cap on or off as desired. Because of the size of socket 16 relative to the cap, the cap is capable of being retained within socket 16 when working with the open tube.

FIG. 2 demonstrates apparatus 10 transitioning from being unattached to pipettor 30 to a positioned attached to pipettor 30 at overhang rim 34. Body 11 is moving towards pipettor 30 in the direction of the arrow. As such, overhang rim 34 is slid between the opening of the U-shaped clasp formed from prongs 12 and 13. Prongs 12 and 13 being of resilient material move from their non-attached positions so as to substantially conform to overhang rim 34. Body 11 continues to move towards pipettor 30 until apparatus 10 comes to its final attached position on handle 31 as shown in FIG. 3.

Figure 5:
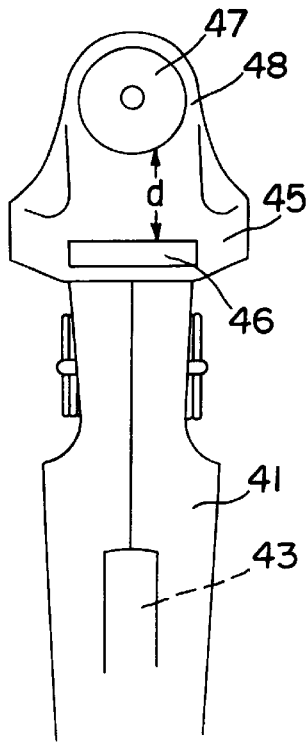
FIG. 5 is a front view of a pipettor having an integrated microcentrifuge tube opener.
Figure 6:
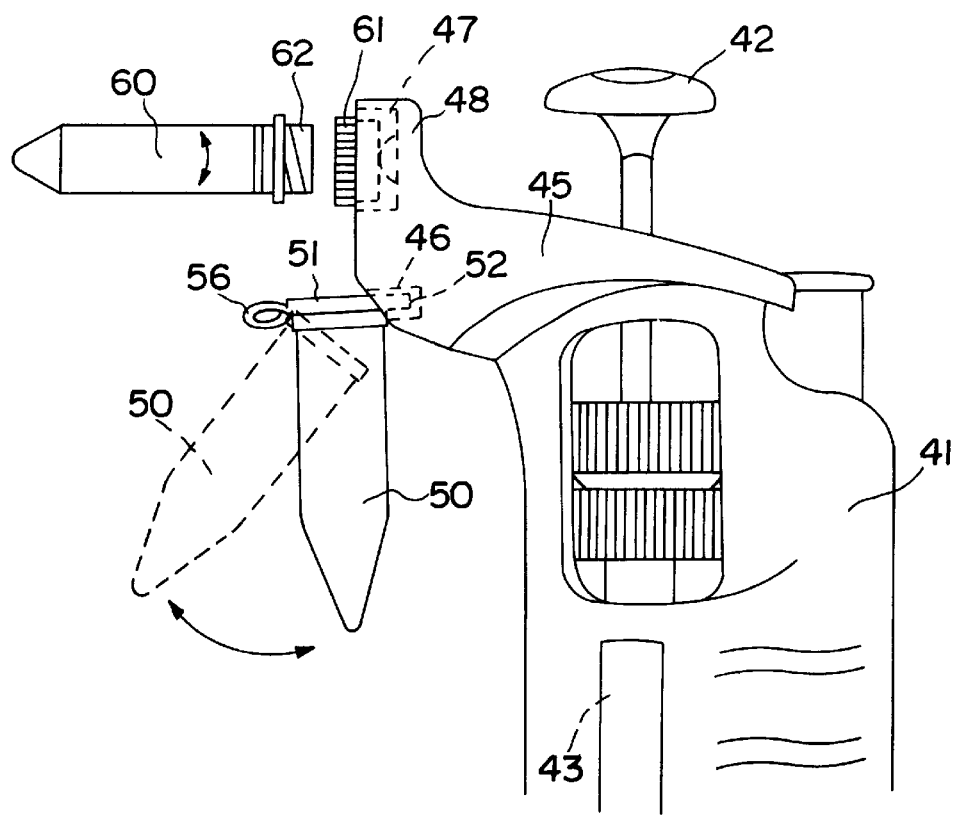
FIG. 6 is a side view of a pipettor having an integrated microcentrifuge tube opener with two microcentrifuge tubes in the process of being opened.

FIGS. 4 through 6 are of pipettor 40 including an integrated microcentrifuge tube opener. As described previously, pipettor 40 has handle 41, plunger 42 and suction shaft 43. Also included as an integrated part of pipettor 40 is at least one microcentrifuge tube opening means formed out of overhanging rim 45. In the embodiment shown, slot aperture 46 is formed out of lower portion of overhang rim 45. Conversely, socket 47 is formed out of raised upper portion 48 of overhanging rim 45. The distance between slot aperture 46 and socket 47, shown as "d" in FIGS. 4 and 5 should create a separation so as to permit the use of both slot aperture 46 and socket 47 on two different tubes simultaneously.

FIG. 6 demonstrates the use of slot aperture 46 and socket 47 simultaneously. Cap 51 is attached at connecting strip 56 to tube 50. Tab 52 of cap 51 is inserted into slot aperture 46. Tube 50 is then swung in the direction of the arrows to an open position as shown in phantom. Of course, it is recognized that tube 50 may remain stationary with pipettor 40 moving relative to tube 50. Alternatively, cap 61 may be inserted into socket 47 within region 48. Socket 47 is again dimensioned so as to be slightly larger in diameter than the diameter of cap 61 thereby creating a friction fit to hold cap 61 stationary and in place. Tube 60 may then be rotated as indicated by the arrows to unscrew from the cap to expose the contents of the tube with the cap being capable of being retained in socket 47. As shown, it is preferable that cap 61 is not inserted entirely into socket 47 so as to minimize contact between tube 60 and upper portion 48 thereby minimizing potential contamination of the contents of tube 60. To close tube 60, threads 62 are aligned with the inner threads of cap 61 and tube 60 is again rotated to screw cap 61 back tightly onto tube 60 thereby sealing the tube, which can then be removed from socket 47.

Figure 7:
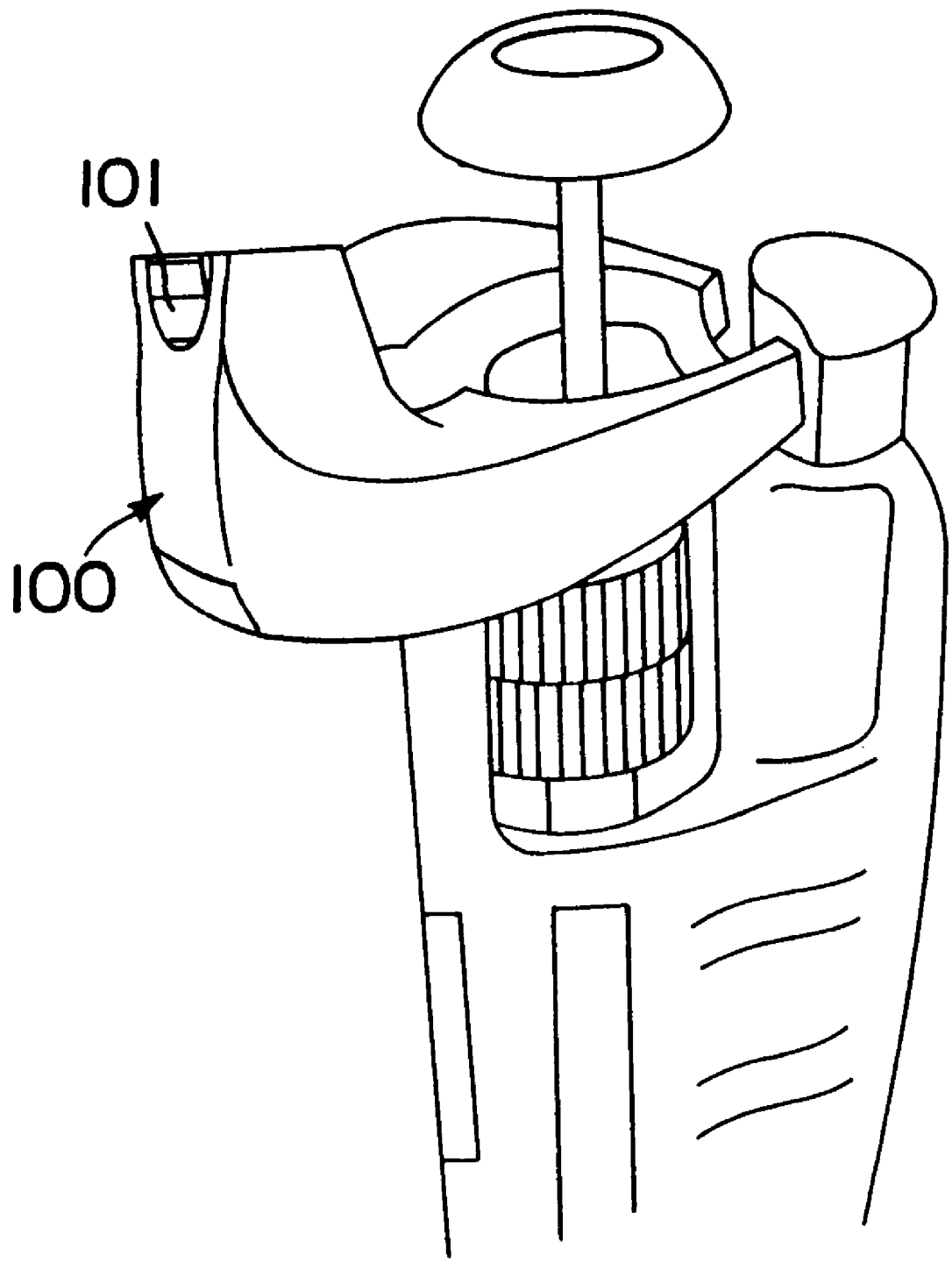
FIG. 7 is a front perspective view of a pipettor having an integrated microcentrifuge tube opener with the cap engagement means comprising a substantially semi-circular socket.

FIG. 7 shows an integrated microcentrifuge tube opener 100 similar in function and operation to the embodiment described above. However in the embodiment, socket 101 is substantially semi-circular in shape.

The foregoing description and drawings merely explain and illustrate the invention and the invention is not limited thereto, except insofar as the appended claims are so limited as those skilled in the art who have the disclosure before them will be able to make modifications and variations therein without departing from the scope of the invention.

I claim:

1. A pipettor attachable microcentrifuge tube opening apparatus for the opening of a microcentrifuge tube by removing a cap from said microcentrifuge tube so as to permit access to the contents of said microcentrifuge tube by a pipettor, said pipettor attachable microcentrifuge tube opening apparatus comprising:

a body having a pipettor attachment region on one end of said body and a tube opener region positioned on an opposite end of said body thereto;

said pipettor attachment region having securement means for restraining said microcentrifuge tube opening apparatus to said pipettor; and a cap engagement means operably positioned within said tube opener region for receipt of at least a portion of said cap of said microcentrifuge tube so as to restrain said cap in position when said tube is being opened.

2. A pipettor attachable microcentrifuge tube opening apparatus according to claim 1 in which said securement means comprises a pair of semi-flexible prongs forming a substantially U-shaped clasp, said pipettor being moved through an opening formed by said U-shaped clasp so said pipettor is at least partially encircled by said pair of semi-flexible prongs to, in turn, restrain said microcentrifuge tube opening apparatus in position on said pipettor.

3. A pipettor attachable microcentrifuge tube opening apparatus according to claim 1 wherein said cap engagement means comprises a slot aperture operably positioned within said tube opener region for receipt of at least a portion of a tab portion of said cap to, in turn, restrain the position of said cap as said cap is moved in a direction away from said microcentrifuge tube so as to open said microcentrifuge tube.

4. A pipettor attachable microcentrifuge tube opening apparatus according to claim 3 wherein said tube opener region being substantially perpendicular to said attachment region within said body thereby creating an upper end and a lower end within said tube opener region so that said lower end contains said slot aperture and is adjacent to said attachment region of said body, said tube opener region further includes a second cap engagement means operably positioned proximate said upper end of said tube opener region.

5. A pipettor attachable microcentrifuge tube opening apparatus according to claim 4 wherein said second cap engagement means comprises a substantially semi-circular socket operably positioned for receipt of at least a portion of said cap's outer perimeter, where said semi-circular socket being dimensioned to have a diameter slightly larger than said cap for frictional receipt of said cap's outer perimeter to, in turn, restrain the position of said cap within said socket as said microcentrifuge tube is rotated about a longitudinal axis so as to open said microcentrifuge tube.

6. A pipettor attachable microcentrifuge tube opening apparatus according to claim 4 wherein said second cap engagement means comprises a substantially circular socket operably positioned for insertion of said cap's outer perimeter, where said circular socket being dimensioned to have a diameter slightly larger than said cap's outer for frictional receipt of said cap perimeter to, in turn, restrain the position of said cap within said socket as said microcentrifuge tube is rotated about a longitudinal axis so as to open said microcentrifuge tube.

7. A pipettor attachable microcentrifuge tube opening apparatus according to claim 6 in which said securement means comprises a pair of semi-flexible prongs forming a substantially U-shaped clasp, said pipettor being moved through an opening formed by said U-shaped clasp so said pipettor is at least partially encircled by said pair of semi-flexible prongs to, in turn, restrain said microcentrifuge tube opening apparatus in position on said pipettor.

8. A pipettor attachable microcentrifuge tube opening apparatus according to claim 1 wherein said cap engagement means comprises a substantially semi-circular socket operably positioned for receipt of at least a portion of said cap's outer perimeter, where said semi-circular socket being dimensioned to have a diameter slightly larger than said cap for frictional receipt of said cap perimeter to, in turn, restrain the position of said cap within said socket as said microcentrifuge tube is rotated about a longitudinal axis so as to open said microcentrifuge tube.

9. A pipettor attachable microcentrifuge tube opening apparatus according to claim 1 wherein said cap engagement means comprises a substantially circular socket operably positioned for insertion of said cap's perimeter, where said circular socket being dimensioned to have a diameter slightly larger than said cap for frictional receipt of said cap's outer perimeter to, in turn, restrain the position of said cap within said socket as said microcentrifuge tube is rotated about a longitudinal axis so as to open said microcentrifuge tube.

10. A pipettor integrated with a microcentrifuge tube opener for the opening of a microcentrifuge tube by removing a cap, from said microcentrifuge tube so as to permit access to the contents of said microcentrifuge tube by said pipettor, said pipettor comprising:

a longitudinal handle, a plunger and a suction shaft for insertion into said microcentrifuge tube towards dispensing or removing fluids from said tube;

said handle having a top and bottom end and being operably positioned between said plunger and said suction shaft so that said plunger is adjacent to said top end of said handle and operably connected to said suction shaft positioned adjacent said bottom end of said handle; and said handle further including at least one microcentrifuge tube cap engagement means operably positioned within said handle for receipt of at least a portion of said microcentrifuge tube cap, so as to restrain said cap in position when said tube is being opened.

11. A pipettor integrated with a microcentrifuge tube opener according to claim 10 wherein said at least one microcentrifuge tube engagement means is formed out of an overhanging rim of material about said top end of said handle, said rim includes at least one slot aperture operably positioned within said rim for receipt of at least a portion of a tab portion of said cap to, in turn, restrain the position of said cap as said cap is moved in a direction away from said tube so as to open said microcentrifuge tube.

12. A pipettor integrated with a microcentrifuge tube opener according to claim 10 wherein said at least one microcentrifuge tube engagement means is formed out of an overhanging rim of material about said top end of said handle, said rim includes at least one substantially semi-circular socket operably positioned for receipt of at least a portion of said cap's outer perimeter, where said semi-circular socket being dimensioned to have a diameter slightly larger than said cap for frictional receipt of said cap's outer perimeter to, in turn, restrain the position of said cap within said socket as said microcentrifuge tube is rotated about a longitudinal axis so as to open said microcentrifuge tube.

13. A pipettor integrated with a microcentrifuge tube opener according to claim 10 wherein said at least one microcentrifuge cap opener means is formed out of an overhanging rim of material about said top end of said handle, said rim includes at least one substantially circular socket operably positioned for insertion of said cap's outer perimeter, where said circular socket being dimensioned to have a diameter slightly larger than said cap for frictional receipt of said cap perimeter to, in turn, restrain the position of said cap within said socket as said microcentrifuge tube is rotated about a longitudinal axis so as to open said microcentrifuge tube.

14. A pipettor integrated with a microcentrifuge tube opener according to claim 10 wherein said at least one microcentrifuge tube cap engagement means comprises a first and second microcentrifuge tube cap engagement means;

said first microcentrifuge tube cap engagement means being formed out of an overhanging rim of material about said top end of said handle, said rim includes at least one slot aperture operably positioned within said rim for receipt of at least a portion of a tab portion of said cap to, in turn, restrain the position of said cap as said microcentrifuge cap is moved in a direction away from said tube so as to open said microcentrifuge tube; and said second microcentrifuge tube cap engagement means being operably positioned within a raised upper portion on said rim, said raised upper portion being substantially perpendicular to said rim and substantially parallel to said handle.

15. A pipettor integrated with a microcentrifuge tube opener according to claim 14 in which said second microcentrifuge tube cap engagement means comprises a substantially semi-circular socket operably positioned for receipt of at least a portion of said outer cap's perimeter, where said semi-circular socket being dimensioned to have a diameter slightly larger than said cap for frictional receipt of said cap perimeter to, in turn, restrain the position of said cap within said socket as said microcentrifuge tube is rotated about a longitudinal axis so as to open said microcentrifuge tube.

16. A pipettor integrated with a microcentrifuge tube opener according to claim 14 in which said second microcentrifuge tube cap engagement means comprises a substantially circular socket operably positioned for insertion of said cap's perimeter, where said circular socket being dimensioned to have a diameter slightly larger than said cap for frictional receipt of said cap's outer perimeter to, in turn, restrain the position of said cap within said socket as said microcentrifuge tube is rotated about a longitudinal axis so as to open said microcentrifuge tube.

* * * * *